United States Patent [19]

Murakami et al.

[11] Patent Number: 4,575,441
[45] Date of Patent: Mar. 11, 1986

[54] EXHAUST GAS SENSOR AND PROCESS FOR PRODUCING SAME

[75] Inventors: Nobuaki Murakami, Nishinomiya; Katsuyuki Tanaka, Suita; Kousuke Ihokura, Takarazuka, all of Japan

[73] Assignee: Figaro Engineering Inc., Japan

[21] Appl. No.: 587,530

[22] Filed: Mar. 8, 1984

Related U.S. Application Data

[62] Division of Ser. No. 482,239, Apr. 5, 1983, Pat. No. 4,459,577.

[30] Foreign Application Priority Data

Apr. 17, 1982 [JP]  Japan .................................. 57-64209

[51] Int. Cl.$^4$ .............................................. H01L 7/00
[52] U.S. Cl. ........................................ 264/61; 264/115
[58] Field of Search ................... 264/61, 115; 73/23, 73/27 R; 338/34; 422/98

[56] References Cited

U.S. PATENT DOCUMENTS

| | | | |
|---|---|---|---|
| 3,886,785 | 6/1975 | Stadler | 73/23 |
| 4,033,169 | 7/1977 | Fujishiro et al. | 422/96 |
| 4,066,413 | 1/1978 | Segawa et al. | 422/98 |
| 4,228,128 | 10/1980 | Esper et al. | 422/98 |
| 4,260,978 | 4/1981 | Yasuda et al. | 338/34 |
| 4,287,751 | 9/1981 | Yasuda et al. | 73/23 |

FOREIGN PATENT DOCUMENTS 2908916  9/1980  Fed. Rep. of Germany .......... 73/23

Primary Examiner—James Derrington
Attorney, Agent, or Firm—Kane, Dalsimer, Kane, Sullivan and Kurucz

[57] ABSTRACT

A combustion gas sensor and material therefore responsive to changes in the composition of ambient atmospheres wherein the sensing element includes $SnO_2$ crystals having a mean $\bar{d}$ of approximately 500–3200 Å and having a surface area to mass ratio S of 1–8 m$^2$/g a process for making same. Preferably, the standard deviation of crystal size distribution is $0.2\bar{d}$.

10 Claims, 14 Drawing Figures

No b42×40000

No b4×30000

— b4(900°C)
--- c1(900°C)
—·— b2(900°C)
—··— b41(900°C)

⊙ b4
△ b5
◇ b41
▣ b6

EXHAUST GAS SENSOR AND PROCESS FOR PRODUCING SAME

This is a division, of application Ser. No. 482,239, filed Apr. 5, 1983, now U.S. Pat. No. 4,459,577.

BACKGROUND OF THE INVENTION

The present invention relates to improvements in combustion gas sensors having $SnO_2$ incorporated therein and a process for producing same. More particularly the invention relates to exhaust gas sensors wherein use is made of the fact that the electrical conductivity of $SnO_2$, varies with the composition of ambient atmospheres, i.e. $O_2$, $CO$, and $H_2$ concentrations.

DESCRIPTION OF THE PRIOR ART

Sensors responsive to changes in the composition of ambient atmospheres have various applications and have been found particularly useful in devices for regulating the air/fuel ratios in combustion type devices, eg. furnaces, space heaters, internal combustion engines, etc., to optimize fuel efficiency, reduce pollution, and the like.

For example, it is well known that the operation of an internal combustion engine produces substantial quantities of deleterious gaseous by-products. The principal pollutants so produced are hydrocarbons, carbon monoxide and various oxides of nitrogen. Extensive investigations have led to the discovery that the use of a catalytic converter within the exhaust system of an internal combustion engine provides a practical technique for reducing the emission of the deleterious gaseous by-products.

A catalytic exhaust gas treatment device, or 'converter', which is capable of converting the principal pollutants into water, carbon dioxide, and gaseous nitrogen is often referred to as a "three-way catalyst". For the three-way catalyst devices to be most effective, the exhaust gases introduced into the converter for treatment must be the product of the combustion of a substantially stoichiometric air/fuel ratio. Assuming that $\lambda$ is the stoichiometric air/fuel ratio the region where the converter is most effective extends from about $0.99\lambda$ to about $1.01\lambda$.

In view of the narrowness of the region wherein the catalytic converter is most effective, it has been determined that the associated internal combustion engine must be operated with a combustible mixture as close as possible to stoichiometric equivalence.

To assure continuous or substantially continuous operation at the optimum air/fuel ratio, it has been proposed to employ sensors responsive to the chemistry of the exhaust gases. One known type of exhaust gas sensor employs a ceramic material which demonstrates a predictable electrical resistance change when the composition of the exhaust gas changes. An example of such a material is titania (titanium dioxide having a general formula $TiO_2$). Such sensors may be fabricated in accordance with the teachings of U.S. Pat. No. 3,886,785 issued to Stadler et al., titled "Gas Sensor and Method of Manufacture".

Such exhaust gas sensors are also useful for preventing incomplete combustion. For example, air or space heaters, furnaces and like combustion type devices may be regulated to avoid incomplete combustion by detecting the composition of the exhaust gas from the device with an exhaust gas sensor and associated means for altering the air/fuel mixture accordingly.

Published Unexamined Japanese Patent Application No. 55099/1978 corresponding U.S. Pat. No. 4,194,994; and West German Patent Application No. 2,648,373 disclose an exhaust gas sensor employing $SnO_2$ (stannic oxide). These publications disclose an exhaust gas sensor, which is prepared by admixing a small amount of $Nb_2O_5$ or $MgO$ with $SnO_2$ and calcining the mixture at about 650° to 850° C. These sensors exhibit marked variations in electrical conductivity in response to variations oxygen partial pressure in ambient atmospheres at about 600° C.

Published Unexamined Japanese Patent Application No. 19592/1976 and corresponding U.S. Pat. No. 4,033,169 and West German Patent Application No. 2,535,500 disclose that the sensitivity of $SnO_2$ to hydrocarbons decreases greatly at temperatures greater than about 300° C.

Exhaust gas sensors must withstand both oxidizing atmospheres and reducing atmospheres, while they are not infrequently heated to temperatures of about 900° C. This means that the exhaust gas sensor must be resistant to various atmospheres at high temperatures.

Furthermore, the exhaust sensors must be rapidly responsive and highly sensitive to changes in atmospheres.

Because exhaust gas sensors are heated by exhaust gases, they often experience temperatures that vary over the range of about 400° to 900° C. in accordance with variations in the combustion conditions concerned and the design of the particular device. It is therefore preferred that exhaust gas sensors be operable over a wide temperature range and that the resistivity of sensors be less dependent on the temperature to assure higher detection accuracy.

It is also desirable that exhaust gas sensors transmit large input signals to the circuits connected thereto, consequently, it is desirable to reduce the overall resistivity of the sensor itself.

SUMMARY OF THE INVENTION

An object of the present invention is to provide an exhaust gas sensor which is stable in various atmospheres at high temperatures.

Another object of the invention is to provide an exhaust gas sensor having high sensitivity and rapid responsiveness to changes of atmospheres.

Another object of the invention is to provide an exhaust gas sensor operable a wide range of operating temperatures.

Another object of the invention is to provide an exhaust gas sensor having a low resistance that is not greatly affected by temperature changes.

Still another object of the invention is to provide a process for producing exhaust gas sensors which fulfill the foregoing objects.

It has been discovered that sensors responsive to changes in the $O_2$, $CO$, and/or $H_2$ concentrations in ambient atmospheres may be improved, in accordance with the foregoing objects, by controlling the surface area to mass ratio S, hereinafter defined, and mean crystal size $\bar{d}$, hereinafter defined, in sensing elements containing at least some metal oxide particularly $SnO_2$.

A preferred exhaust gas sensor in accordance with the present invention has incorporated therein a sensing element composed of $SnO_2$ for detecting changes in the composition of ambient atmospheres and is characterized in that the $SnO_2$ sensing element has a 1 to 8 m$^2$/g in surface area ratio S and 3200 to 500 Å mean crystal size $\bar{d}$. An even more preferable range for S is between about 1.4 and 2.5. With the exhaust gas sensor of the present invention, it is especially preferable that the standard deviation of crystal size distribution of the $SnO_2$ be at least $0.2\bar{d}$ based on $d^3N(d)$ wherein d is the size of each crystal and N(d) is the distribution of crystal sizes.

The process of the present invention for producing sensors comprises heating tin or a compound thereof in an non-reducing atmosphere to prepare $SnO_2$ having a surface area S of 1 to 8 m$^2$/g and a mean crystal size d of 3200 to 500 A. $SnO_2$ with a wide distribution of crystal sizes can be prepared from a stannic acid sol which contains anion impurities, such as $Cl^-$, $Br^-$, $I^-$, $F^-$, $NO_3^-$ or $SO_4^{2-}$, by heating the sol in a non-reducing atmosphere to obtain as an intermediate product $SnO_2$ containing such anion impurities in an amount of 0.14 to 0.60 mmol/g.$SnO_2$, and heating the product again to approximately 1000° to 1400° C.

The surface area ratio S herein referred to is a value measured by the B.E.T. method while the mean crystal size $\bar{d}$ is the mean diameter of crystals in the direction of D(1,1,0) plane.

The surface area ratio S and the mean crystal size $\bar{d}$ are thus specified for the following reasons.

There are three kinds of $SnO_2$ materials for exhaust gas sensors.

The first, (hereinafter referred to as "$SnO_2(A)$") is $SnO_2$ having a surface area of at least 10 m$^2$/g and a mean crystal size of up to 400 Å. $SnO_2(A)$, which is used for detecting combustible gases in an atmosphere, is suited for detecting small amounts of combustible gases in the presence of large quantities of oxygen. The characteristics of exhaust gas sensors wherein $SnO_2(A)$ is used alter when the sensor is exposed to a hot reducing atmosphere. If these sensors are exposed to reducing atmospheres at about 900° C. for a prolonged period of time and then to oxidizing atmospheres, their resistivity is lowered permanently and even if heated in the oxidizing atmosphere for a long period of time, the material fails to return to its initial resistivity. When $SnO_2(A)$ is exposed to a reducing atmosphere for shorter periods of time, the resistivity thereof suffers hysteresis, such that the material exhibits a temporarily reduced resistivity when subsequently exposed to an oxidizing atmosphere. Moreover, this material demonstrates reduced rates of response to changes from reducing atmospheres to the oxidizing atmospheres.

The second, (hereinafter referred to as "$SnO_2(C)$") is $SnO_2$ having a surface area of up to 0.7 m$^2$/g and a mean crystal size of at least 5000 Å. Since preparation of $SnO_2(C)$ involves accelerated crystal growth resulting in decreased proportions of defects in the crystals, the material is higher in resistivity and in temperature coefficient of resistance. $SnO_2(C)$ also has reduced surface activity and is therefore low in sensitivity and in responsiveness. Although calcined at a high temperature, $SnO_2(C)$ is prone to crystal growth and has low resistance to heat. For example, when heated at 900° C., the material exhibits an irreversibly altered resistivity in an oxidizing atmosphere. Stated more specifically, heating in an oxidizing atmosphere imparts an increased resistivity to the material, while heating in a reducing atmosphere gives a reduced resistivity to the material.

In contrast, the tin dioxide of the present invention (sometimes referred to herein as "$SnO_2(B)$") which has an S of 1 to 8 m$^2$/g and a $\bar{d}$ of 3200 to 500 Å exhibits outstanding characteristics as a material for exhaust gas sensors. $SnO_2(B)$ is stable under various atmospheres at high temperatures, free from substantial variations in its resistivity with the lapse of time, and rapidly responds to the change from a reducing atmospheres to oxidizing atmospheres. Additionally, $SnO_2(B)$ is highly sensitive and rapidly responsive over a wide temperature range and has a low resistivity which is less dependent on temperature that of the above noted $SnO_2$ types.

These differences in characteristics appear attributable to the following. When subjected to a hot reducing atmosphere, $SnO_2(A)$ wherein the crystals have not grown fully, may be reduced to the interior of its lattice. When the lattice is reduced, sintering proceeds through the reduced portion, resulting in decreased resistance at the interface between the crystals. When the reduced material is placed in an oxidizing atmosphere, hysteresis that is delayed response will result because the interior of the crystals must be reoxidized. $SnO_2(C)$ is susceptible to sintering and is therefore unable to retain its electrical properties after exposure to high temperatures.

For the reasons given above, the $SnO_2(B)$ to be used in this invention is adapted to have an S value of about 1 to 8 m$^2$/g and a d of 3200 to 500 Å.

Preferably, the standard deviation $\sigma(d)$ of the crystal size distribution of the $SnO_2$ is at least $0.2\bar{d}$ based on $d^3N(d)$ wherein $\bar{d}$ is the mean crystal size, d is the size of each crystal and N(d) is the distribution of crystal sizes. Further $d^3$, i.e., the volume of each crystal, is taken as the weight factor of the distribution because what appears to be of significance is the volume or weight ratio of $SnO_2$ of crystal sizes relative to the whole $SnO_2$, rather than the mere number of particles having the crystal sizes.

With $SnO_2$ prepared by a usual method, for example, by thermally decomposing $Sn(CO_2)$ in an oxidizing atmosphere, or by repeatedly washing a stannic acid sol with water to fully remove anion impurities therefrom and calcining the sol, the standard deviation of the crystal sizes is about $0.1\bar{d}$.

However, when a stannic acid sol, containing substantial quantities of anion impurities is calcined the standard deviation of crystal size distribution of the resulting $SnO_2$ may be as great as at least $0.2\bar{d}$. When the electrical characteristics of materials having varying distributions of crystal sizes are compared, it is noted that the wider their distribution, the higher their sensitivity and responsiveness at low temperatures. Accordingly, it is desirable to use $SnO_2$ with a wider crystal size distribution to provide a sensors which perform better over a wider range of temperatures.

The upper limit for crystal size distribution may generally be greater than $0.6\bar{d}$ and is certainly greater than 0.45.

$SnO_2$ having a large distribution of crystal sizes can be prepared from $SnO_2$ having lesser crystal size distributions containing substantial quantities of anion impurities, such as $Cl^-$, $Br^-$, $I^-$, $F^-$, $NO_3^-$ or $SO_4^{2-}$, by heating the material at 1000° to 1400° C. During the heat treatment sometimes referred to as calcining, the anion impurities contained in the material appear to cause a widened distribution of crystal sizes. $SnO_2$ containing a substantial quantity of anion impurities may be obtained by thermally decomposing stannic acid containing at least 0.11 mmol/g.$Sn(OH)_4$ of anion impurities to $SnO_2$. It is critical that the resulting $SnO_2$ intermediate material contain 0.14 to 0.60 mmol/g.$SnO_2$ of anion impurities. With less than 0.14 mmol/g.$SnO_2$ or more than 0.60 mmol/g.$SnO_2$ of impurities present, the $SnO_2$ eventually obtained will have a distribution of crystal sizes less than that preferred in the present invention.

DESCRIPTION OF PREFERRED EMBODIMENTS

EXAMPLE A

A 100 g quantity of metal Sn is added to 800 ml of 6N nitric acid, and the mixture is reacted overnight at about 50° C., giving a stannic acid sol containing a large amount of $NO_3^-$ ions. The reaction mixture is filtered to remove the unreacted residue, the filtrate is placed into a rotary kiln, and the kiln is continuously heated at 300° C. until disappearance of $NO_2$ evolution. The resulting stannic acid gel is heated in air at 600° C. for 2 hours (primary calcination) to obtain $SnO_2$ still containing $NO_3^-$ ions. The primary calcined $SnO_2$ is then pulverized wet in a ball mill for 6 hours, molded into a pellet-shaped ceramic member having a pair of Pt-Rh alloy wires embedded therein, and then heated in air at 1050° to 1350° C. for 2 hours (secondary calcination).

Figure 1:
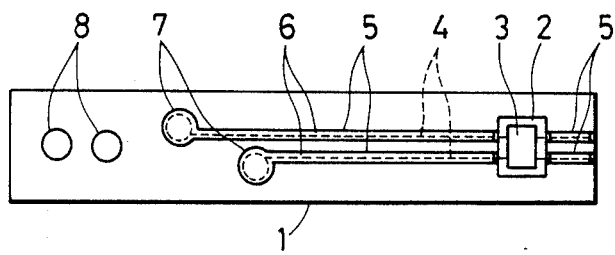
FIG. 1 is a plan view showing the configuration of an exhaust gas sensor embodying the invention.
Figure 2:
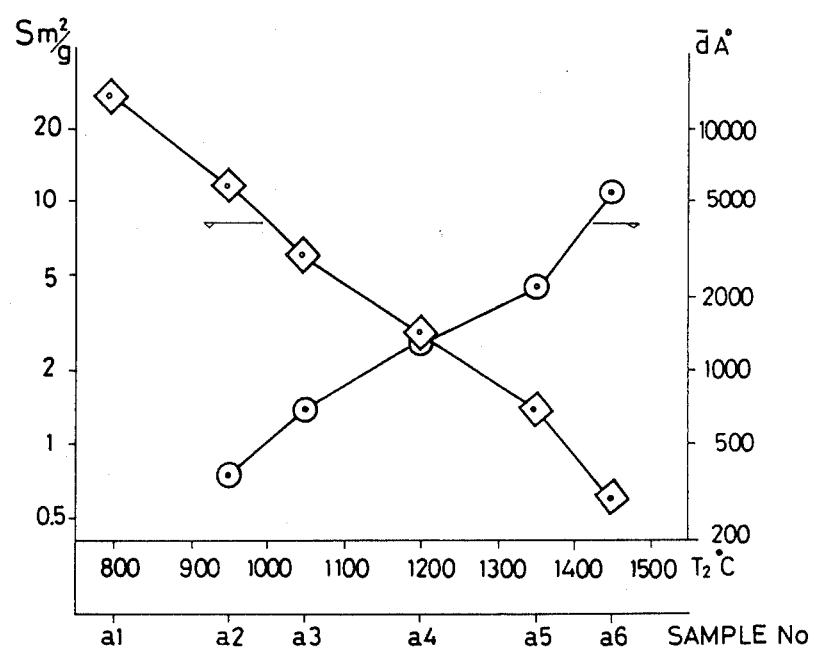
FIG. 2 is a characteristics diagram showing the relation of the secondary calcination temperature $T_2$ (hereinafter defined) to the surface area ratio S as well as with the mean crystal size $\bar{d}$, as determined with samples prepared by reacting metal Sn with nitric acid and subjecting the resulting stannic acid to primary calcination at 600° C.
Figure 3:
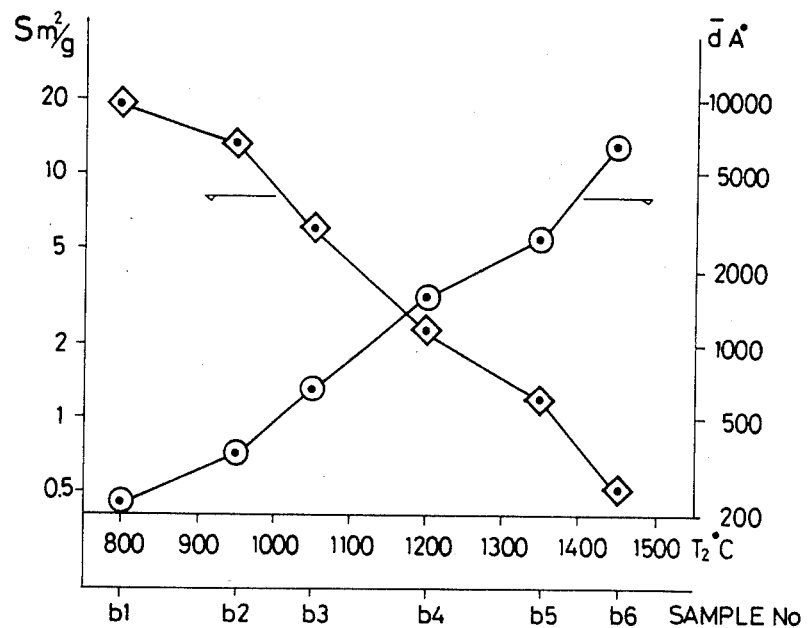
FIG. 3 is a characteristics diagram showing the relation of the secondary calcination temperature $T_2$ with the surface area S as well as with the mean crystal size $\bar{d}$, as determined with samples prepared by hydrolyzing an aqueous solution of $SnCl_4$ with ammonia to obtain a stannic acid sol containing a large amount of $Cl^-$ ions and subjecting the sol to primary calcination at 600° C.
Figure 4:
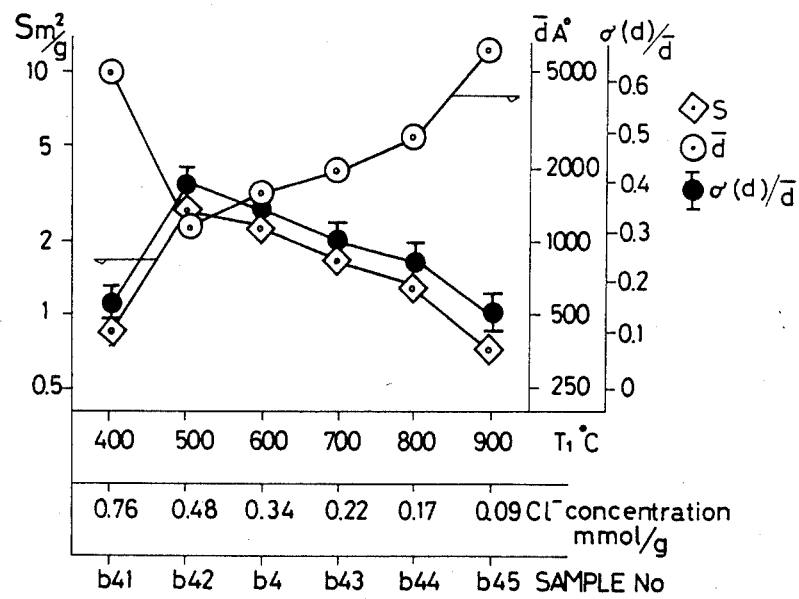
FIG. 4 is a diagram showing characteristics of samples prepared by neutralizing $SnCl_4$ with ammonia to obtain stannic acid containing a large amount of $Cl^-$ ions, subjecting the acid to primary calcination at varying temperatures $T_1$ and further subjecting the products to secondary calcination at 1200° C.
Figure 5:
FIGS. 5 and 6 are electron photomicrographs showing $SnO_2$ samples (not pulverized) prepared from a stannic acid sol containing $Cl^-$ ions.
Figure 6:
Figure 7:
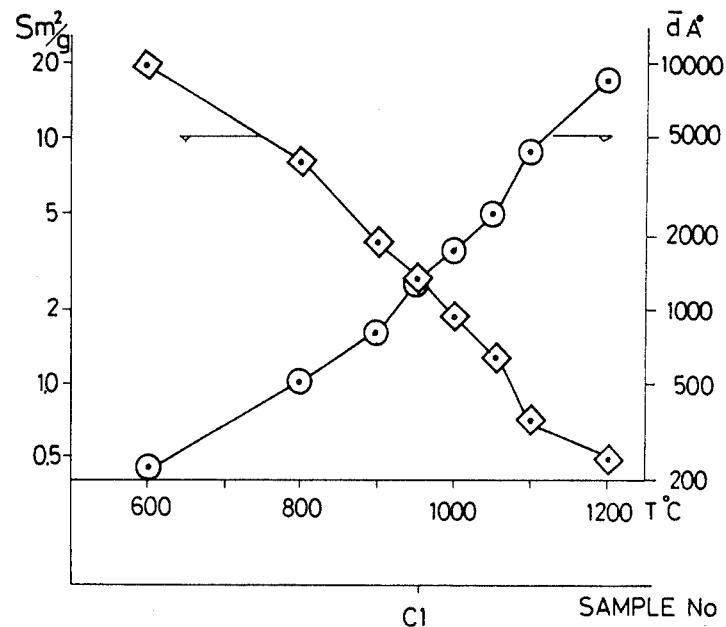
FIG. 7 is a diagram showing the characteristics of a sample prepared by thermally decomposing $Sn(CO_2)_2$ in oxygen.
Figure 8:
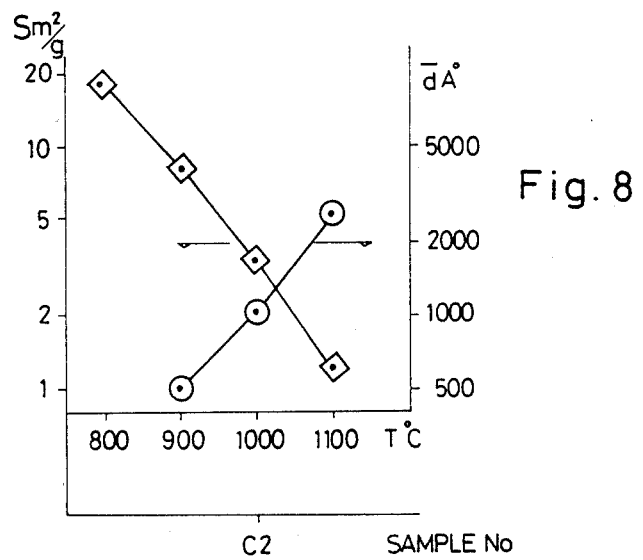
FIG. 8 is a diagram showing the characteristics of a sample prepared by hydrolyzing an aqueous solution of $SnCl_4$ with ammonia to obtain a stannic acid sol, washing the sol with water to completely remove the $Cl^-$ ions and thermally decomposing the sol in air.

The ceramic member obtained is mounted on a support member to fabricate an exhaust gas sensor shown in FIG. 1. With reference to this drawing, indicated at 1 is the support member which is made of a base plate of alumina or like ceramic. The support member 1 is formed with a hole 2 close to its forward end. The ceramic element 3, i.e., the $SnO_2$ pellet, is accommodated in the hole 2. The $SnO_2$ ceramic element 3 may further incorporate therein various other additives, such as $Al_2O_3$ serving as an aggregate, amorphous silica as a binder for $SnO_2$, and/or Pt, Rh or the like as sensitivity enhancing agents.

It will be appreciated that the additions of binders sensitizing agents and the like as contemplated by the present invention as well as, molding conditions, e.g. pressure, may have some effect on S but experience has shown that these effects are small and insignificant for purposes of this invention seldom exceeding 10%. A pair of Pt-Rh alloy wires embedded in the ceramic member 3 to serve as output electrodes 4 which conduct current from the ceramic element 3 and may also support the ceramic member 3 within hole 2. The wires comprising electrodes 4 extend thru a pair of elongated grooves 5 formed in the support member 1 to retain the ceramic element 3 in the hole 2. Preferably electrodes 4 are held in grooves 5 by an inorganic adhesive 6. The base ends of the alloy wire electrodes 4 are connected to metal pins 7 for electrically connecting the electrodes to an external circuit. A pair of holes 8 may be provided in support member 1 for attaching the sensor to a combustion chamber, or the like, by any suitable means such as bolts and nuts.

The $SnO_2$ may be subjected to secondary calcination first, then pulverized and thereafter molded into a ceramic element 3 about electrodes 4 that extend into grooves 5 on both sides of hole 2 as shown in FIG. 1. Thus the ceramic element 3 may be fixed to the support member 1 at four points, with the electrode wires 4 protected by the inorganic adhesive 6. Samples of $SnO_2$ or of exhaust gas sensors thus prepared will be designated "A1" to "A6".

EXAMPLE B

Anhydrous $SnCl_4$ (250 g) is dissolved in 1 liter of water, the solution is neutralized with 300 ml. of 15N ammonia water, and the reaction mixture is allowed to stand overnight at room temperature to obtain a matured stannic acid sol. With addition of 1 liter of water, the reaction mixture is centrifuged, and the supernatant is discarded. The stannic acid sol thus obtained contains a substantial quantity of $Cl^-$ and is thereafter heated to 350° C. in a rotary kiln to prepare a stannic acid gel. This step evaporates the excess of ammonia, dehydrates the sol, and sublimes $NH_4Cl$. The gel is then calcined and fashioned into an exhaust gas sensor in the same manner as described above in Example A. Samples of $SnO_2$ or of exhaust gas sensors thus prepared will be designated "B1" to "B6" and "B41" to "B45".

EXAMPLE C1

$Sn(CO_2)_2$ is heated in an oxygen atmosphere at 600° to 1200° C. for 3 hours to obtain $SnO_2$, which is used for fabricating an exhaust gas sensor of the construction shown in FIG. 1. $Sn(CO_2)$ is used as the starting material to avoid the influence of anion impurities.

EXAMPLE C2

Anhydrous $SnCl_4$ (250 g) is added to 1 liter of water and neutralized with 300 ml of 15N ammonia water, and the reaction mixture is allowed to stand overnight at room temperature. With addition of 1 liter of water, the mixture is centrifuged. This centrifuging procedure is repeated until the $Cl^-$ concentration of the supernatant is reduced to below the lower limit detectable with silver nitrate test paper. The resulting stannic acid sol is heated in air at 800° to 1100° C. to obtain $SnO_2$, which is fabricated into an exhaust gas sensor of the construction shown in FIG. 1. Although the aqueous $SnCl_4$ solution is neutralized with $NH_3$ in the above process, $NH_3$ may be replaced by a substance, such as $(NH_4)_2CO_3$, which releases $NH_3$ on reacting with the $SnCl_4$ solution.

Table 1 shows the S, $\bar{d}$ and $\sigma(d)/\bar{d}$ values of the typical samples characterized by FIGS. 2 to 7.

TABLE 1

Surface Areas and Crystal Sizes of Samples

| Sample No. | S (m²/g) | $\bar{d}$ (Å) | $\sigma(d)/\bar{d}$ |
| --- | --- | --- | --- |
| A1[1] | 27 | 150 | |
| A2 | 12 | 370 | |
| A3 | 6.0 | 700 | 0.35 |
| A4 | 2.9 | 1300 | |
| A5 | 1.4 | 2200 | |
| A6 | 0.6 | 5500 | |
| B1[2] | 20 | 220 | 0.45 |
| B2 | 13.5 | 350 | |
| B3 | 6.0 | 650 | 0.35 |
| B4 | 2.3 | 1600 | |
| B5 | 1.2 | 2700 | 0.25 |
| B6 | 0.5 | 6500 | 0.15 |
| B41 | 0.84 | 5000 | 0.15 |
| B42 | 2.7 | 1100 | 0.4 |
| B4* | 2.3 | 1600 | 0.35 |
| B43 | 1.7 | 1900 | 0.3 |
| B44 | 1.3 | 2700 | 0.25 |
| B45 | 0.72 | 6500 | 0.15 |
| C1[3] | 2.8 | 1300 | 0.1 |
| C2[4] | 3.4 | 1100 | 0.1 |

*The data for the same sample is listed again for the purpose of description.
[1] A stannic acid sol prepared by reacting metal Sn with nitric acid is used as the starting material for the group a (A1 to A6).
[2] A stannic acid sol containing $Cl^-$ ions is used as the starting material for the group B (B1 to B6, B41 to B45). For the samples B1 to B6, the primary calcination temperature is 600° C., and the secondary calcination temperature is 800 to 1450° C. For the samples B41 to B45, the primary calcination temperature is 400 to 900° C., and the secondary calcination temperature is 1200° C.
[3] Prepared by thermally decomposing $Sn(CO_3)$ at 950° C.
[4] Prepared by thermally decomposing a stannic acid sol, free from $Cl^-$, at 1000° C.

EFFECT OF PULVERIZATION

Samples were pulverized wet in a ball mill for 24 hours. Table 2, showing the results, reveals that with the samples within the scope of the present invention, secondary particles only were broken, i.e. the crystals per se remaining unbroken. Electron photomicrographs of some of the pulverized samples indicate that the top portions of primary crystals are broken to produce fine crystals, which nevertheless exert no substantial influence on $\bar{d}$.

TABLE 2

| | Effect of Pulverization | |
| --- | --- | --- |
| Sample No. | Before pulverization $\bar{d}$ (Å) | After Pulverization $\bar{d}$ (Å) |
| A3 | 700 | 700 |
| B2 | 350 | 350 |
| B3 | 650 | 650 |
| B5 | 2700 | 2700 |
| B6 | 6500 | 6000 |
| B43 | 1900 | 1900 |

HEAT RESISTANCE

Samples were heated at 900° C. for 72 hours in combustion product atmospheres derived from air/fuel ratios where $\lambda=1.1$ or $\lambda=0.9$ where $\lambda$ is the stochimetric point as hereinabove described. Table 3 shows the resulting variations in d, indicating that greater variations occurred in $\bar{d}$ at $\lambda=0.9$, i.e. reducing atmosphere, than at $\lambda=1.1$, i.e. oxidizing atmosphere. The heat resistance of the samples is not always proportional to the final calcination temperature. The samples A6 and B6 for which full crystal growth has been effected are more susceptible to variations. The samples B41 and B45, which have been subjected to the same final calcination as the sample B4, are also prone to variations. The foregoing is summarized in Table 3 below.

TABLE 3

Variations In d Due To Heating

| | $\bar{d}$ (Å) | | | |
| --- | --- | --- | --- | --- |
| | $\lambda = 0.9$ | | $\lambda = 1.1$ | |
| Sample No. | Before test | After test | Before Test | After Test |
| A2 | 370 | 500 | 370 | 370 |
| A3 | 700 | 700 | 700 | 700 |
| A5 | 1300 | 1300 | 1300 | 1300 |
| A6 | 5500 | 7000 | 5500 | 6000 |
| B1 | 220 | 400 | 220 | 250 |
| B2 | 350 | 600 | 350 | 350 |
| B3 | 650 | 700 | 650 | 650 |
| B4 | 1600 | 1600 | 1600 | 1600 |
| B5 | 2700 | 2700 | 2700 | 2700 |
| B6 | 6500 | 8000 | 6500 | 7000 |
| B41 | 5000 | 7000 | 5000 | 5500 |
| B45 | 6500 | 8000 | 6500 | 700 |

This data suggests that the problems associated with the durability of exhaust gas sensors is attributable to hot reducing atmospheres and that the problem can be overcome by the use of $SnO_2$ wherein crystal growth is suitably inhibited rather than by the use of $SnO_2$ wherein relatively uninhibited crystal growth has been permitted.

RESISTIVITY, TEMPERATURE COEFFICIENT OF RESISTANCE AND SENSITIVITY

Figure 9:
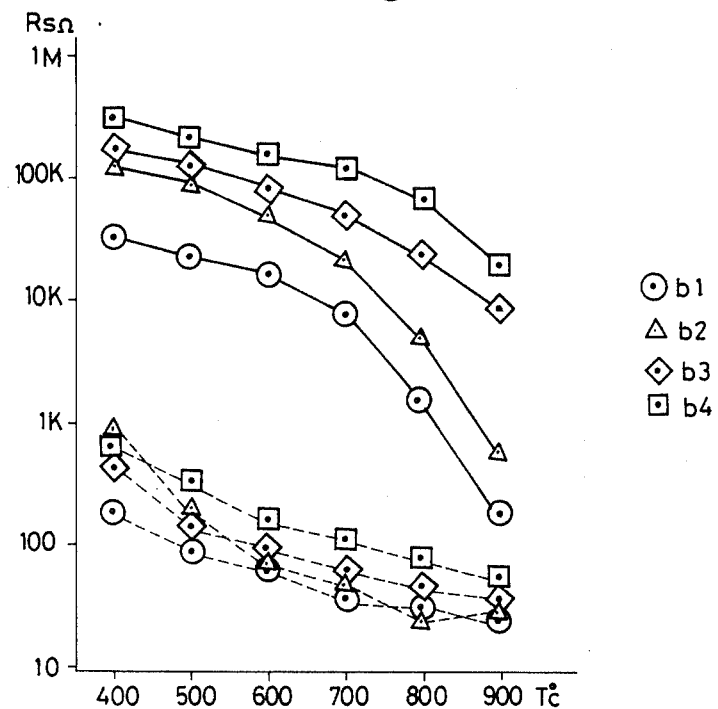
FIGS. 9 to 11 are characteristics diagrams showing the resistivities of exhaust gas sensors in an oxidizing atmosphere (solid lines) and in a reducing atmosphere (broken lines).
Figure 10:
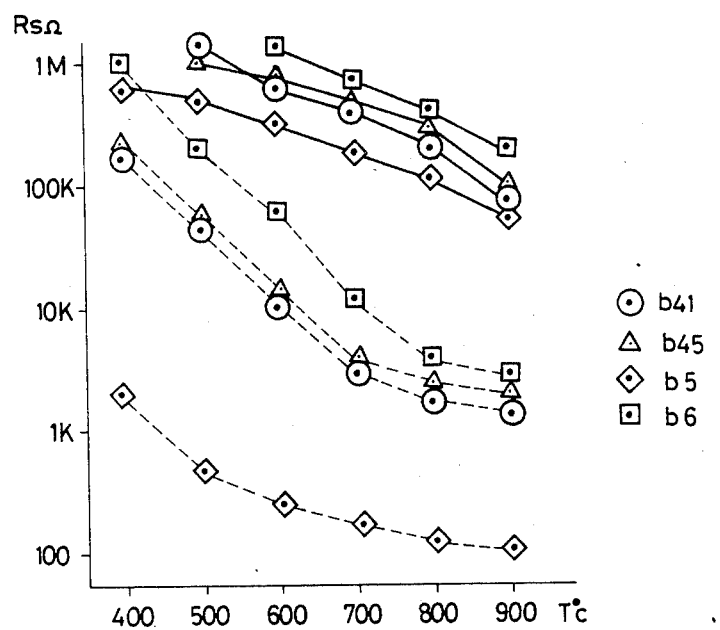
Figure 11:
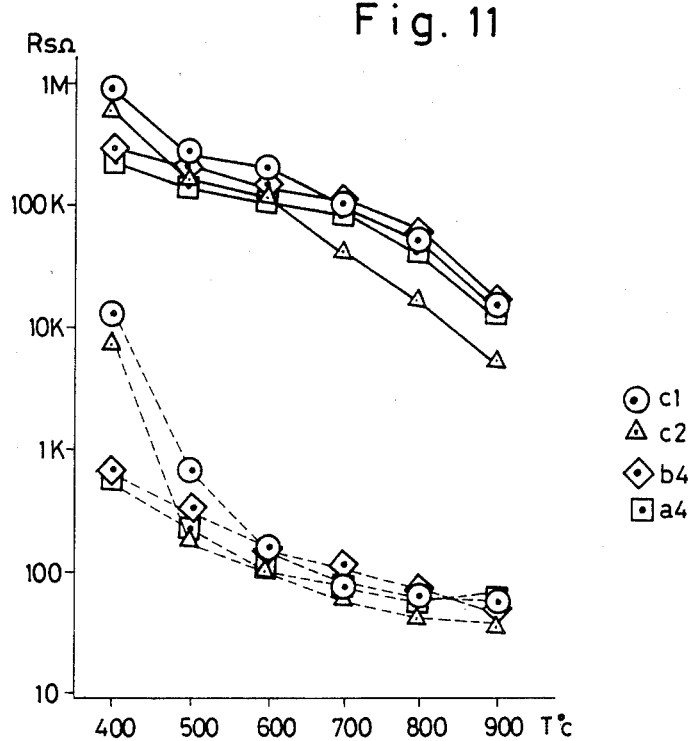

FIGS. 9 to 11 show the resistivities, temperature coefficients of resistance and sensitivities of various samples. In these drawings, the solid line represents resistivities at $\lambda=1.1$, and the broken line those at $\lambda=0.9$. The distance between the solid line and the broken line represents the sensitivity to the change of atmospheres. The results achieved with the samples B1 to B4 (FIG. 9) show that the samples are not much different in resistivity at $\lambda=0.9$ but differ in resistivity at $\lambda=1.1$. At $\lambda=1.1$, the resistivity of the exhaust gas sensor increases with the growth of crystals, and this tendency becomes more pronounced at higher temperatures. If the ratio between the resistivities at $\lambda=1.1$ and $\lambda=0.9$ is considered to be sensitivity, then sensitivity improves with crystal growth, especially at higher temperatures.

FIG. 10 shows the results achieved with an exhaust gas sensor (B5) with suitable growth of crystals and exhaust gas sensors (B41, B45 and B6) with excessive crystal growth. In samples with excessive crystal growth, markedly increased resistivities result at $\lambda=0.9$, and reduced sensitivity. Such sensors also exhibit increased resistivities also at $\lambda=1.1$ and are difficult to use at low temperatures.

FIG. 11 shows the results achieved with exhaust gas sensors (B4 and A4) having enlarged in crystal size distribution and an exhaust sensors (C1 and C2) diminished in distribution. Although the samples are not much different in surface area S and mean crystal size d, the samples C1 and C2 are considerably lower in sensitivity than the samples B4 and A4 at 400° C. This indicates that an increased distribution of crystal sizes leads to an enhanced sensitivity at low temperatures.

When the samples of group a (A1 to A6) were made to resemble one another in S and d, the results achieved were similar to those attained with the samples of group B (B1 to B6) and therefore will not be described.

RESPONSIVENESS

Figure 12:
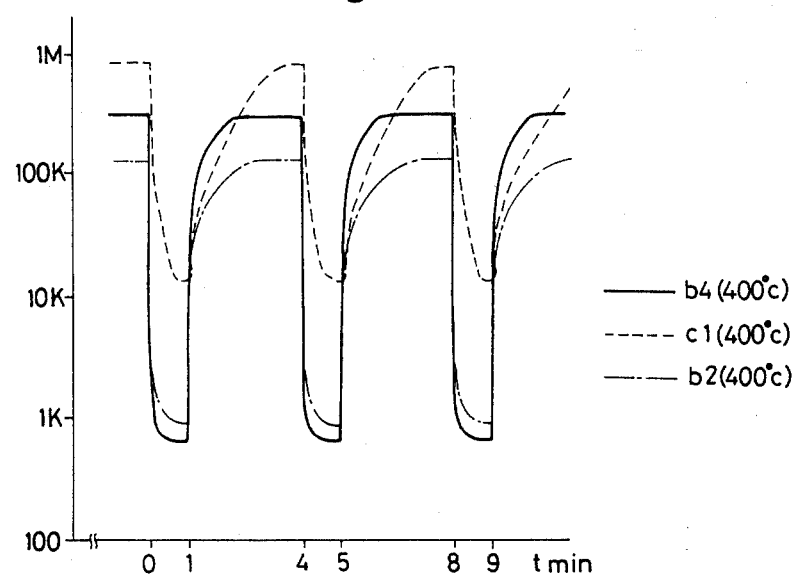
FIGS. 12 and 13 are characteristics diagrams showing the responsiveness of exhaust gas sensors to changes of atmospheres.
Figure 13:
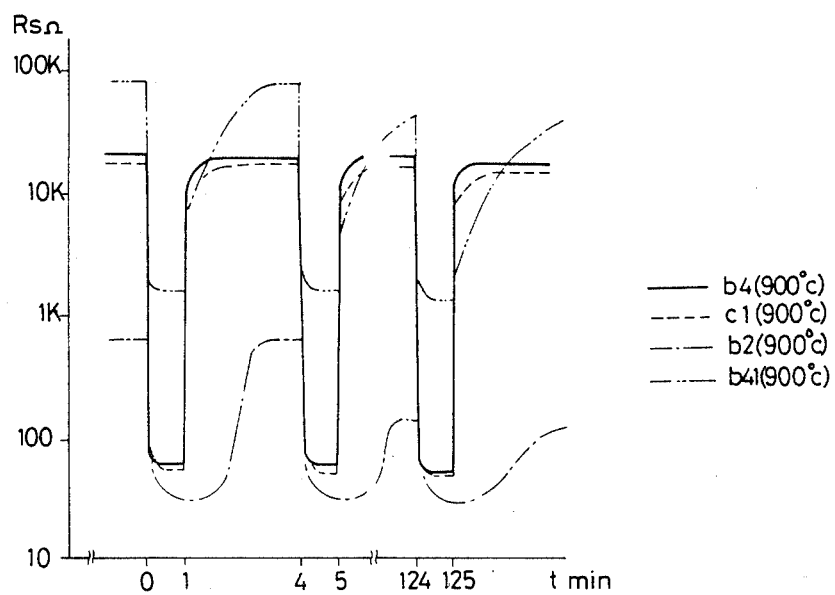

FIGS. 12 and 13 show the responsiveness of exhaust gas sensors to the change of $\lambda$ from 1.1 to 0.9. The sensors used were B4 and C1 as typical examples embodying the invention, B2 as an example with insufficient crystal growth, and B41 as an example with excessive crystal growth. At 400° C. (FIG. 12), B4 is similar to B2 in responsiveness, whereas C1 is delayed in response. The samples B4 and C1 differ in crystal size distribution but are otherwise similar. It is seen that a widened crystal size distribution results in improved responsiveness at low temperatures. No data is shown for B41 because it was difficult to determine the responsiveness thereof at 400° C. due to its high resistivity.

At 900° C. (FIG. 13), B4 and C1 are rapid and similar in response, whereas B2 and B41 are slower in response. The sensor B2 requires more than 1 minute before starting to respond to a change to the oxidizing atmosphere. When subjected to repeated cycles of $\lambda=1.1$ and $\lambda=0.9$, the resistivity at $\lambda=1.1$ decreases to about ¼ the level (at the 32nd cycle starting at 124th minute). On the other hand, B41 is merely slow in the mode of response, starting to respond immediately, and suffers lesser hysteresis when repeatedly subjected to the cycle of $\lambda=1.1$ to $\lambda=0.9$. The above phenomena are not limited to specific samples only; other samples are also subject to such phenomena depending on their S's and mean crystal size $\bar{d}$.

VARIATIONS IN RESISTIVITY DUE TO EXPOSURE TO REDUCING ATMOSPHERES

Table 4 shows variations in the resistivity of exhaust gas sensors resulting from exposure to an atmosphere at 900° C. and $\lambda=0.9$.

When exposed to the above atmosphere for 1 minute (Test (1)), the samples B1, B2 have great difficulty in restoring the initial resistivity even if $\lambda$ is restored to 1.1. This corresponds to the lag preceding the start of response and shown in FIG. 13. The samples B6, B41 and B45, although slow in restoring their resistivity, do not involve such a lag.

When exposed to the reducing atmosphere for 10 minutes (Test (2)), the samples B1 and B2 with insufficient crystal growth and those B6, B41 and B45 with excessive crystal growth all undergo hysteresis in resistivity, exhibiting reduced resistivities even one hour after the change of $\lambda$ to 1.1.

When exposed to the reducing atmosphere for 12 hours (Test (3)), the samples B1, B2, B6 B41 and B45 fail to restore the initial resistivity at $\lambda=1.1$. Even 3 days after the return of $\lambda$ to 1.1, the sample B2, for example, restores the resistivity only to 70% of the initial level. This sample is inherently low in sensitivity at high temperatures and is therefore influenced greatly by the variation of resistivity.

TABLE 4

| | Variations in Resistivity Due To Exposure To Reducing Atmosphere*[1] | | | | | |
|---|---|---|---|---|---|---|
| | Test (1) | Test (2) | | Test (3) | | |
| Sample No. | In 1 min. | In 10 min | In 1 hr. | In 10 min | In 1 day | In 3 days |
| A3 | 0.8 | 0.96 | 0.99 | 0.98 | 0.97 | 1.02 |
| A4 | 0.98 | 0.99 | 1.01 | 0.97 | 0.97 | 1.01 |
| A5 | 0.8 | 0.95 | 1.01 | 0.98 | 0.99 | 0.99 |
| B1° | 0.1 | 0.2 | 0.3 | 0.1 | 0.5 | 0.6 |
| B2° | 0.1 | 0.3 | 0.45 | 0.15 | 0.6 | 0.7 |
| B3 | 0.7 | 0.9 | 0.99 | 0.9 | 0.97 | 0.99 |
| B4 | 0.97 | 1.02 | 0.99 | 0.98 | 1.01 | 0.99 |
| B5 | 0.8 | 0.95 | 1.01 | 0.92 | 0.98 | 0.98 |
| B6° | 0.4 | 0.55 | 0.6 | 0.3 | 0.7 | 0.9 |
| B41° | 0.44 | 0.6 | 0.7 | 0.3 | 0.7 | 0.9 |
| B42 | 0.98 | 0.98 | 1.01 | 0.97 | 0.99 | 1.03 |
| B4*[2] | 0.97 | 1.02 | 0.99 | 0.98 | 1.01 | 0.99 |
| B43 | 0.9 | 1.01 | 0.99 | 0.95 | 0.98 | 0.97 |
| B44 | 0.8 | 0.96 | 1.00 | 0.92 | 0.97 | 0.98 |
| B45° | 0.4 | 0.6 | 0.7 | 0.3 | 0.7 | 0.9 |

*[1]The sensor is disposed within an apparatus maintained at 900° C. and $\lambda = 1.1$, and the atmosphere is temporarily changed to $\lambda = 0.9$. The result is given in terms of the ratio of the resistivity of the sample as measured after the atmosphere is thereafter returned to $\lambda = 1.1$, to the resistivity before the exposure to the reducing atmosphere. The duration of exposure to the reducing atmosphere is 1 minute for Test (1), 10 minutes for Test (2) and 12 hours for Test (3).
*[2]The data for the same sample is given for the purpose of description.
°The mark "°" indicates a comparison example.

Although it appears that the samples B6, B41 and B45 generally return to their initial resistivity, these samples have a tendency to exhibit an increased resistivity when heated at $\lambda=1.1$ at 900° C., so that the apparent data will not be indicative of the restoration of the resistivity.

CHARACTERISTICS IN HOT OXIDIZING ATMOSPHERE DETERMINED WITH LAPSE OF TIME

Figure 14:
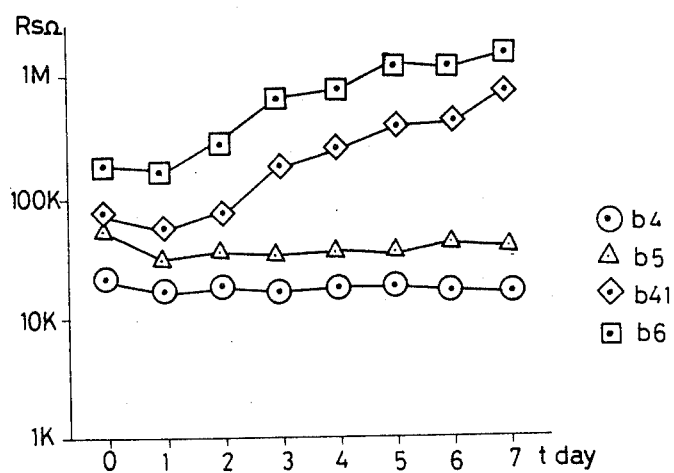
FIG. 14 is a characteristics diagram showing variations in the resistivity of exhaust gas sensors at 900° C. in an oxidizing atmosphere.

FIG. 14 shows variations in the resistivity of sensors when they are exposed to an atmosphere at $\lambda=1.1$ at 900° C.

With the sensors B4 and B5, the resistivity decreases during the first day and thereafter levels off, whereas with the sensors B41 and B6, the resistivity steadily increases without any tendency to level off. In view of the fact that the sensors B41 and B6 originally have a high resistivity, these sensors do not appear useful even if the resistivity could be stabilized to a constant level with a lapse of time.

OPERATION OF THE EXHAUST GAS SENSOR

Sensors constructed in accordance with this invention may be used to regulate the air/fuel ratio in combustion type devices such as combustion engines, space heaters, furnaces, and the like. For example, the sensor may be placed in the exhaust pipe of an internal combustion engine wherein it is heated to operating temperatures between 400° and 900° C. The composition of exhaust gases passing through the exhaust pipe is primarily a function of the air/fuel ratio. The electrical resistance of the sensor changes in response to changes in the exhaust gas composition causing the magnitude of a control signal from the sensor to vary. A suitable electromechanical means is provided to adjust the air/fuel ratio in accordance with the magnitude of the control signal.

What is claimed is:

1. A process for producing combustion gas sensor elements, which comprise:

heating a composition including at least one member of the group consisting of tin and tin compounds in a non-reducing atmosphere to produce $SnO_2$ crystals having a d, wherein d is the mean particle size, of approximately 500-3200 Å and an S, wherein S is the surface area per unit mass, of approximately 1-8 $m^2/g$;

pulverizing the $SnO_2$ into a ceramic element; and, molding the pulverized $SnO_2$ into a ceramic element; and providing the ceramic element with means for connection to an electric circuit.

2. The process for producing combustion gas sensor elements defined in claim 1, further comprising:

admixing at least one component selected from the group consisting of alumina, amorphous silica, platinum and rhodium.

3. The process for producing combustion gas sensor elements, defined in claim 1, wherein:

the means for connecting the ceramic element of an electric current comprises a pair of electrodes embedded in the ceramic element.

4. The process for producing combustion gas sensor elements as defined in any one of claims 1, 2, or 3, wherein:

the heating is conducted in two steps comprising:

a primary calicination of the composition in a non-reducing atmosphere in the presence of substantial quantities of anion impurities to produce an $SnO_2$ intermediate containing between about 0.14 and 0.60 mmol/g.$SnO_2$ of the anion impurities, and a secondary calcination of the $SnO_2$ intermediate in a non-reducing atmosphere at temperatures between about 1000° and 1400° C. to produce $SnO_2$ having an S of about 1 to 8 $m^2/g$, a $\bar{d}$ of about 500-3200 Å, and a standard deviation in crystal size distribution of at least $0.2\bar{d}$.

5. The process for producing combustion gas sensor elements defined in claim 4, wherein:

at least one anion impurity is selected from the group consisting of $Cl^-$, $Br^-$, $I^-$, $F^-$, $NO_3^-$ and $SO_4^{-2}$.

6. The process for producing combustion gas sensor elements defined in claim 4, wherein:

the composition is a stannic acid sol containing at least 0.11 mmol/g.$Sn(OH)_4$ anion impurity.

7. The process for producing combustion gas sensor elements defined in claim 6, wherein:

the stannic acid sol is prepared by dissolving tin metal in nitric acid.

8. The process for producing combustion gas sensor elements defined in claim 6, wherein:

the stannic acid sol is prepared by hydrolyzing an aqueous solution containing $Sn^{+4}$ ions with at least one member selected from the group consisting of ammonia and compounds thereof.

9. The process for producing combustion gas sensor elements defined in claim 6, wherein:

the primary calcination step includes dehydrating the stannic acid sol to an acid gel and further heating the gel in a non-reducing atmosphere at 450°-800° C. thereby producing $SnO_2$.

10. The process for producing combustion gas sensor elements defined in claim 5, wherein:

the composition contains $Sn(CO_2)_2$ and the primary calcination is conducted at 800°-1050° C.

* * * * *